United States Patent
Lin et al.

(10) Patent No.: US 11,419,349 B2
(45) Date of Patent: Aug. 23, 2022

(54) PET FOOD WITH VISIBLE PARTICLES AND PROCESS FOR MAKING SAME

(71) Applicant: Hill's Pet Nutrition, Inc., Topeka, KS (US)

(72) Inventors: Hungwei Lin, Lawrence, KS (US); Dennis Jewell, Lawrence, KS (US); Jennifer Macleay, Topeka, KS (US)

(73) Assignee: Hill's Pet Nutrition, Inc., Topeka, KS (US)

( * ) Notice: Subject to any disclaimer, the term of this patent is extended or adjusted under 35 U.S.C. 154(b) by 219 days.

(21) Appl. No.: 16/732,394

(22) Filed: Jan. 2, 2020

(65) Prior Publication Data

US 2020/0138060 A1 May 7, 2020

Related U.S. Application Data

(62) Division of application No. 15/034,447, filed as application No. PCT/US2013/068407 on Nov. 5, 2013, now Pat. No. 10,548,339.

(51) Int. Cl.
*A23K 50/42* (2016.01)
*A23K 40/25* (2016.01)
*A23K 40/20* (2016.01)
*A23K 20/174* (2016.01)
*A23K 20/147* (2016.01)

(52) U.S. Cl.
CPC ............ *A23K 40/25* (2016.05); *A23K 20/147* (2016.05); *A23K 20/174* (2016.05); *A23K 40/20* (2016.05); *A23K 50/42* (2016.05)

(58) Field of Classification Search
CPC ........ A23K 40/20; A23K 40/25; A23K 50/40; A23K 50/42; A23K 20/147; A23K 20/174
See application file for complete search history.

(56) References Cited

U.S. PATENT DOCUMENTS

| | | |
|---|---|---|
| 4,454,163 A | 6/1984 | Gellman et al. |
| 4,551,343 A | 11/1985 | Gellman et al. |
| 4,743,459 A | 5/1988 | Gellman et al. |
| 4,743,461 A | 5/1988 | Gellman et al. |
| 5,480,673 A | 1/1996 | Rokey |
| 5,891,502 A | 4/1999 | Heck et al. |
| 6,190,591 B1 | 2/2001 | van Lengerich |
| 6,254,910 B1 | 7/2001 | Paluch |
| 6,904,870 B2 | 6/2005 | Russell-Maynard et al. |
| 7,662,414 B1 | 2/2010 | Lawlor |
| 7,977,319 B1 | 7/2011 | Levine |
| 8,114,454 B2 | 2/2012 | Clark et al. |
| 8,158,179 B2 | 4/2012 | Bouvier et al. |
| 9,192,588 B2 | 11/2015 | Kawashima et al. |
| 2003/0099759 A1 | 5/2003 | Cheuk et al. |
| 2003/0175387 A1 | 9/2003 | English |
| 2006/0188611 A1 | 8/2006 | Unlu et al. |
| 2008/0160084 A1 | 7/2008 | Huynh et al. |
| 2008/0233244 A1 | 9/2008 | Swenson |
| 2010/0104691 A1 * | 4/2010 | Bouvier .................. A23P 30/34 426/19 |
| 2010/0112136 A1 * | 5/2010 | Ward ..................... A23K 50/40 426/72 |
| 2011/0117067 A1 * | 5/2011 | Esteghlalian .......... G16B 30/20 424/93.21 |
| 2012/0282369 A1 | 11/2012 | Pandur et al. |
| 2013/0302469 A1 | 11/2013 | Marcussen et al. |
| 2013/0302499 A1 | 11/2013 | Lund et al. |

FOREIGN PATENT DOCUMENTS

| | | | |
|---|---|---|---|
| JP | H03-240445 | 10/1991 | |
| WO | 2012/092391 | 7/2012 | |
| WO | WO-2012100991 A1 * | 8/2012 | ............. A23K 10/16 |

OTHER PUBLICATIONS

International Search Report and Written Opinion in International Application No. PCT/US2013/068407, dated Aug. 1, 2014.
Yorkietalk.com, 2009, "Response from Blue Buffalo regarding lifesource bits . . . " YorkieTalk.com Forum posted Jan. 10, 2009, accessed Mar. 6, 2013.
Zinn, R. A. 2004, "A Guide to Feed Mixing", U of CA, Davis.

* cited by examiner

*Primary Examiner* — Walter A Moore

(57) ABSTRACT

The invention provides dry pet food diet compositions that include visible micronutrient particles comprising micronutrients, and improved methods for their preparation. The methods provide pet food diet compositions that have improved palatability and retention of micronutrients.

8 Claims, No Drawings

PET FOOD WITH VISIBLE PARTICLES AND PROCESS FOR MAKING SAME

CROSS-REFERENCE TO RELATED APPLICATIONS

This application is a divisional of U.S. patent application Ser. No. 15/034,447, which was filed on May 4, 2016, which is a national stage entry of PCT/US2013/068407, which was filed on Nov. 5, 2013. The content of the priority applications are hereby incorporated by reference in their entirety into the present application, to the extent that it is not inconsistent with the present application.

FIELD

The present invention relates to pet food compositions containing visible micronutrient particles. The compositions have enhanced palatability and nutrient visualization, and can be formulated to be delayed-release, resulting in increased efficacy of nutrient delivery.

BACKGROUND

Fortification of pet food by the inclusion of micronutrients such antioxidants, minerals, vitamins, carotenoids, glucosamine, chondroitin sulfate, nutraceutical ingredients and nutrient supplements is an efficient way to sustain and improve the health of companion animals. However, the conventional ways of incorporating micronutrients in dry pet foods do not manifest any indication to either the pets or their owners regarding the physical presence of the micronutrients. Thus, the only indication that such nutrients are present is the label statement appearing on the package.

Pet foods containing separate nutrient-containing particles are known. However, physical segregation or selective consumption between different kinds of kibbles may cause uneven intake of the fortified nutrients. Such externally incorporated nutrient bits are mixed among regular dry pet food kibbles and may tend to segregate from the others upon transportation due to density and/or conformation differences. In addition, some pets may have selective consumption of one kind of kibble. Both situations may lead to inconsistent intakes of the fortified nutrients between the consumptions of food. Thus there is a need for novel pet food compositions and for methods of their manufacture that overcome these problems. This invention is directed to these, as well as other important ends.

SUMMARY

Unless otherwise indicated, the terms "%" or "percent" when used in connection with an ingredient of the compositions of the invention is intended to refer to the percent by weight of the indicated ingredient in the composition.

In one aspect, the invention provides a pet food composition comprising a plurality of kibbles, where the kibbles include one or more micronutrient particles incorporated therein, which micronutrient particles are visually distinct and comprise elevated concentrations of one or more micronutrients, e.g. wherein the concentration of said micronutrient is higher in the micronutrient particles than in the rest of the kibble, e.g., at least 10, 20 or 50 times higher.

In some embodiments, the micronutrient particles include one or more micronutrients selected from antioxidants, minerals, vitamins, carotenoids, glucosamine, chondroitin sulfate, nutraceutical ingredients and nutrient supplements.

In some embodiments of the pet food compositions of the invention, the micronutrient particles are delayed-release particles.

In some embodiments, the micronutrient particles are encapsulated.

In some embodiments of the pet food compositions of the invention, the kibbles contain the micronutrient particles in an amount of up to 10% by weight, or up to 5% by weight, or from 1% to 5% by weight, or from 1% to 4% by weight, or 2% to 4% by weight of the pet food composition.

In some embodiments of the pet food compositions of the invention, the micronutrient particles are a different color than the kibbles, for example.

The present invention also provides methods for producing kibbles that include one or more micronutrient particles incorporated therein, which micronutrient particles are visually distinct and include one or more micronutrients, which comprises the step of mixing micronutrient particles which comprise one or more micronutrients together with an extrudate, and immediately extruding the mixture. In some such embodiments, the extrudate is pre-conditioned prior to mixing with the micronutrient particles.

In some embodiments, the methods comprise the steps of:
a) providing a composition comprising pet food raw materials, wherein the particle size of the raw materials is suitable for extrusion;
b) preconditioning the pet food composition to produce an extrudate;
c) mixing micronutrient particles which comprise one or more micronutrients together with the extrudate; and
d) extruding the mixture.

In some embodiments, the extrusion of step d) is performed immediately after the mixing according to step c).

In some embodiments, the mixing of the micronutrient particles with the extrudate is performed at a temperature lower than the temperature of the preconditioning.

In some embodiments of the methods of the invention, the micronutrient particles are mixed with the extrudate by air-assisted injection.

DETAILED DESCRIPTION

It has been discovered in accordance with the present invention that pet foods compositions can be prepared that contain kibbles that have incorporated therein visible micronutrient particles. In accordance with the methods of the invention, the visually distinct micronutrient particles (also referred to herein as "visible nutrient bits" or "VNBs") are incorporated into the pet food kibble in a manner that both preserves the activity of nutrients in the micronutrient particles, and also retains the color and shape integrity of the particle so they are distinctly visualizable in the kibble.

The incorporation of visualizable micronutrient particles into the kibble provides several important advantages. For example, the pet owner is assured that the micronutrients are indeed present in the pet food composition. In contrast to food compositions containing different kinds of kibbles, it is much more difficult for the incorporated particles to become physically segregated from the remainder of the kibble. Moreover, it is more difficult for the companion animal to selectively avoid consuming the micronutrients in the micronutrient particles, and the inclusion of micronutrient, visualizable particles increases the palatability of the food composition. The micronutrients can be provided at tightly controlled levels and distributed homogenously throughout the food, and the interactions between micronutrients and other food ingredients are reduced.

Thus, in some embodiments, the present invention provides pet food kibbles including one or more micronutrient particles incorporated therein, wherein the micronutrient particles are visually distinct and include one or more micronutrients.

A wide variety of micronutrients can be incorporated into the kibbles of the invention, including for example and not limitation, one or more antioxidants, minerals, vitamins, carotenoids, nutraceutical ingredients and nutrient supplements, for example glucosamine and/or chondroitin sulfate.

In some embodiments, the micronutrient particles may comprise a medicine. It is difficult to feed medicine to pet. Ideally, a maintenance diet containing wholesome nutrients will be suitable as the carrier for the medicine delivery. Due to the quantitative precision of the VNB technology, the pet food kibbles can be formulated to include a precise dosage of a drug. A kibble containing VNBs, wherein the VNBs comprise a drug, is a feasible and convenient way to deliver medicine for pets on a quantitative manner.

In some embodiments of the pet food compositions of the invention, the micronutrient particles are delayed-release particles. Such delayed-release particles can be manufactured by, for example, processing protein rich ingredients such as corn gluten meal and yeast along with the target nutrients and other components of the micronutrient particle. After processing, these micronutrient particles can be digestively more slowly inside the animal's digestive system than typical pet foods, thus extending the time of release of the micronutrient nutrients or other components.

In general, the kibbles of the pet food compositions of the invention can contain the VNBs in an amount of up to 10% by weight, or up to 5% by weight, or from 1% to 5% by weight, or from 1% to 4% by weight, or 2% to 4% by weight of the pet food composition.

The VNBs of the pet food compositions of the invention are preferably formulated to include one or more coloring agents, such that the VNBs have a color that is distinct from the kibble in which it is incorporated. Preferably, the color, specific shade or color, or both of the micronutrient particles are chosen such that the micronutrient particles are distinctly visualized by both a companion animal and its owner.

The incorporation of the VNBs into the pet food compositions of the invention is accomplished in a manner such that the color and shape integrity of the particles is preserved through the extrusion process, resulting in incorporation of VNBs that are visible in the resulting kibbles. For example, in one embodiment, a typical pet food processing apparatus is employed having a live bottom holding bin into which the raw mix is fed. The raw mix is then transported via a variable speed feeder screw to a preconditioner, where liquids including but not limited to water, fat or oil, nutrients, additive, and steam are added and the raw mix is preconditioned. After preconditioning, the conditioned mix (partially hydrated hot mix) is directed into the extruder barrel. In accordance with the methods of the invention, the micronutrient particles are added into the stream of hot mix immediately prior to the mix entering the extruder barrel. Adding the micronutrient particles into the mix at a point after preconditioning is complete ensures that the VNBs will not be subjected to the high temperatures and relatively extreme conditions of the preconditioning, and also minimizes the exposure to excessive hydration or mechanical stress, thus preserving their physical integrity.

The VNBs can be added to the mix by any effective means. One preferred method of addition is by air-assisted injection, for example by using a side feeding device that allows for direct addition of an air stream carrying VNBs into the mix. One such device employs a tube that has at one end (a) an inlet for compressed air configured to create an air stream in the tube, and a valve for regulating the flow thereof; at the other end (b) an injection nozzle that is inserted into the mix line at or near the head of the extrusion barrel; and (c) a hopper for holding the micronutrient particles is located in between (a) and (b), wherein the particles are fed from the hopper into the air stream. In one embodiment, the diameter of the inlet for compressed air stream is narrowed from 10% to 60% before opening to the outlet pipe near the bottom of the hopper in order to create a very focused air stream approximately perpendicular to the vertical axis of the hopper, which draws the particles out of the bottom of the hopper. The amount of VNBs fed into the extruder can be quantitatively controlled by, for example a feeder device such as those manufactures by Acrison, Inc., Moonachie, N.J. The VNBs can be dosed into the hopper of the side feeding device by the feeder and then injected into the extruder via a stream of compressed air, thus reducing hydrothermal and mechanical stresses exerted on the VNBs and promoting their mixing into the stream.

Thus, the present invention also provides methods for producing kibbles that include one or more micronutrient particles incorporated therein, which micronutrient particles are visually distinct and include one or more micronutrients, which comprises the step of mixing micronutrient particles which comprise one or more micronutrients together with an extrudate, and immediately extruding the mixture. In some such embodiments, the extrudate is pre-conditioned prior to mixing with the micronutrient particles.

In some embodiments, the methods comprise the steps of a) providing a composition comprising pet food raw materials, wherein the particle size of the raw materials is suitable for extrusion; b) preconditioning the pet food composition to produce an extrudate; c) mixing micronutrient particles which comprise one or more micronutrients together with the extrudate; and d) immediately extruding the mixture.

As discussed above, raw pet food mix compositions are typically subjected to a preconditioning process that can include subjecting the mix to humid conditions at elevated temperatures. Such preconditioning can impair the nutritional value of many nutrients such as vitamins, carotenoids, antioxidants, etc. Addition of VNBs containing such nutrients into the feed mix after preprocessing, and preferably as close to the head of the extruder barrel as possible, protects the nutrients in the VNBs from excessive exposure to thermal and hydrolytic conditions, and improves the retention of micronutrients.

The invention thus provides, in one embodiment, a pet food composition (Composition 1) comprising a plurality of kibbles, where the kibbles include one or more micronutrient particles incorporated therein, which micronutrient particles are visually distinct and include one or more micronutrients, for example:
- 1.1. Composition 1, wherein the micronutrient particles include one or more micronutrients selected from antioxidants, minerals, vitamins, carotenoids, glucosamine, chondroitin sulfate, nutraceutical ingredients and nutrient supplements.
- 1.2. Any foregoing composition wherein the micronutrient particles include one or more micronutrients selected from antioxidants, minerals, vitamins, carotenoids, glucosamine, chondroitin sulfate, nutraceutical ingredients, nutrient supplements and/or medicines.

1.3. Any foregoing composition wherein the micronutrient is a compound which is labile under heat and/or moisture conditions normally occurring in manufacture of kibble.
1.4. Any foregoing composition wherein the micronutrient particle comprises an extrudable binder, e.g., comprising gluten and/or rice.
1.5. Any foregoing composition wherein the micronutrient particle comprises one or more micronutrients, one or more pigments, and an extrudable binder.
1.6. Any foregoing composition wherein the micronutrient particles are delayed-release particles.
1.7. Any foregoing composition wherein the micronutrient particles are evenly distributed in the composition, e.g., wherein the coefficient of variance (CV) for distribution of a micronutrient provided in the micronutrient particles in the composition is less than 10%.
1.8. Any foregoing composition wherein the micronutrient particles are encapsulated.
1.9. Any foregoing composition wherein the composition is produced in accordance with any of Method 1, et seq. below.
1.10. Any foregoing composition wherein the micronutrient particles have approximately the same density as the kibbles, e.g., wherein the ratio of the density of the kibble material to the density of the microparticle is 2:1 to 1:2, e.g., about 1:1.
1.11. Any foregoing composition wherein the kibbles contain the micronutrient particles in an amount of from 1% to 10%, e.g., 2% to 5% by weight of the pet food composition.
1.12. Any foregoing composition wherein the micronutrient particles are a different color than the kibbles, for example red.
1.13. Any foregoing composition wherein the micronutrient particles are from 0.5-10 mm in size, e.g. 1-4 mm in size.
1.14. Any foregoing composition where the micronutrient particles comprise ascorbic acid and/or thiamine.
1.15. Any foregoing composition where the micronutrient particles comprise rice and/or wheat gluten.
1.16. Any foregoing composition where the micronutrient particles comprise flavoring and coloring.
1.17. Any foregoing composition wherein the micronutrient particles comprise one or more orally acceptable pigments, e.g., iron oxide, in an amount effective to impart color to the micronutrient particle.
1.18. Any foregoing composition wherein the micronutrient particle comprises a flavorant or palatability enhancer, e.g., bacon flavor.
1.19. Any foregoing composition where the micronutrient particles comprise brewers rice, wheat gluten, ascorbic acid and thiamine.
1.20. Any foregoing composition wherein the micronutrient particles have significantly different composition from the rest of the kibble, e.g., comprise at least 100 times the concentration of a particular micronutrient.
1.21. Any foregoing composition where the micronutrient particles comprise:
from 45% to 55% brewers rice;
from 35% to 45% wheat gluten;
from 1% to 5% ascorbic acid; and
from 1% to 5% thiamine hydrochloride.

In yet another embodiment, the invention provides a method (Method1) for making kibbles for use in a pet food composition, wherein the kibbles include one or more micronutrient particles incorporated therein, which micronutrient particles are visually distinct and include one or more micronutrients, e.g., a pet food composition according to any of Composition 1, et seq., supra, comprising the step of mixing micronutrient particles which comprise one or more micronutrients together with an extrudate, and immediately extruding the mixture, for example,
1.1. Method 1, wherein the extrudate is pre-conditioned prior to mixing with the micronutrient particles.
1.2. Any foregoing method comprising the steps of:
a) providing a composition comprising pet food raw materials, wherein the particle size of the raw materials is suitable for extrusion;
b) preconditioning the pet food composition to produce an extrudate;
c) mixing micronutrient particles which comprise one or more micronutrients together with the extrudate; and
d) extruding the mixture.
1.3. The method of 1.2 wherein the mixture in step d) is extruded immediately after mixing according to step c).
1.4. Any foregoing method wherein the mixing of the micronutrient particles with the extrudate is performed at a temperature lower than the temperature of the preconditioning.
1.5. Any foregoing method wherein the micronutrient particles are mixed with the extrudate by air-assisted injection.
1.6. Any foregoing method wherein the micronutrient particles are made by mixing ingredients comprising one or more micronutrients, one or more pigments and an extrudable binder, extruding the micronutrient mixture thus obtained, grinding the micronutrient extrudate thus obtained to provide micronutrient particles of the desired size, and drying the micronutrient particles.

The following examples are further illustrative of the nature of the present invention, but it is understood that the invention is not limited thereto. All amounts and proportions referred to herein and in the appended claims are by weight, unless otherwise indicated.

EXAMPLE 1

Preparation of Pet Food Containing Micronutrient Particles

One significant feature of the pet food compositions of the present invention is the visibility of the micronutrient nutrient-containing particles in the pet food kibbles. Micronutrient particles were made in a different color than the typical food kibble, and incorporated into kibbles using the methods described herein, to minimize the thermal and hydrolytic processing of the mix containing the micronutrient particles. Pet food compositions were prepared incorporating either 2% or 4% of the micronutrient particles into a commercial canine adult dry formula.

Micronutrient particles were prepared having the following composition:

| Component | Percent by Weight |
| --- | --- |
| Rice, Brewers | 49 |
| Wheat, Gluten | 40 |
| Ascorbic acid, usp, fine, granular | 2.5 |
| Thiamine hydrochloride | 2.5 |

-continued

| Component | Percent by Weight |
|---|---|
| Sweet Bacon Flavor | 3 |
| Red Iron Oxide Solution | 3 |

The micronutrient particles were processed using a typical extrusion process for dry pet foods. After extrusion, the semi-dried kibbles were collected from the extrusion line then ground coarsely. The resulting particles were sieved and collected in between 1 mm and 4 mm screens, i.e., so that the particles were between 1 and 4 mm in size. The collected portion was dried using a hot air oven then stored under ambient conditions until use. These micronutrient particles (dried color bits) are herein referred to as "Visible Nutrient Bits" or "VNBs".

The canine adult dry formulation was made with inclusion of either 2% or 4% by weight of VNBs added to the feed line through a window in the connection duct between the pre-conditioner and the extruder barrel, using an air assisted delivering devise as described above. The amount of VNBs fed into the extruder was quantitatively controlled by an Acrison feeder. VNBs were dosed into the hopper of the side feeding device by the Acrison feeder and then injected into the extruder via a stream of compressed air.

The appearance of VNBs on the surface of dried kibbles of the canine adult dry formulation was examined visually. As expected, the non-VNB included Control did not show any apparent red bits on the kibble surface, while the red VNBs appeared vividly on the surface of kibbles containing either 2% or 4% of the VNBs. It was observed that the red VNBs appeared on every kibble of the 4% VNB included formula, but not necessarily on the every kibble of the 2% VNB included formula. From these results, it is believed that the inclusion of approximately 4% VNB is sufficient to result in visible VNBs on each kibble of the pet food composition.

EXAMPLE 2

Nutrient Distribution

Another important feature of the pet food compositions of the invention is that the incorporation of micronutrient particles throughout the kibbles provides even distribution of fortified micronutrients among individual kibbles so that the companion animal (e.g., cat or dog) will have even intake of micronutrients upon each occasion of food consumption regardless the amount of food intake. This is important, as the differences in eating behavior among different pets (due to factors such as pet sizes, breeds, owner's feeding habits, and the tendency of some pets tend to eat small portions of their food throughout a day, while others consume all designated food during a single meal) can result in under- or over-consumption of micronutrients for pets.

Pet foods containing separate nutrient-containing particles are known. However, physical segregation or selective consumption between different kinds of kibbles may cause uneven intake of the fortified nutrients. Such externally incorporated nutrient bits are mixed among regular dry pet food kibbles and may tend to segregate from the others upon transportation due to density difference. In addition, some pets may have selective consumption of one kind of kibble, and the owner may not take a consistent quantity of the nutrient-containing particles from the package. These situations may lead to inconsistent intakes of the fortified nutrients between the consumptions of food.

In contrast, the pet food compositions of the present invention maintain the visibility of included nutrient bits on kibble surface while offering the benefit of even rationing of the fortified micronutrients from one bite to another regardless pet's eating behavior or owner's feeding habits.

The evenness of a micronutrient distribution in a pet food diet can be expressed by the precision and accuracy of the nutrient incorporation among sample duplicates.

The precision and accuracy of the methods of the invention for distributing micronutrients were determined using manganese (Mn) as an indicator because Mn is usually fortified at small amounts in a diet, which increases the sensitivity of the nutrient distribution study. A canine adult dry formula was prepared without (Control) and including of 3% by weight of VNB. The diets were processed similar to those described above. Ten duplicates of either the non-fortified diet (Control) or 3% VNB included diet (Test) with a sample size of 400 gm for each duplicate were collected randomly during production. Only the minimum amounts of sample were used for Mn analysis in order to maintain the most sensitive detection for the nutrient distribution; therefore, only 5 gm out of each 400 gm sample were used for Mn analysis, which was approximately 12 kibbles per sample.

The evenness of the distribution of fortified micronutrient in a pet food diet can be expressed by the coefficient of variance (CV) of contents of the micronutrient among duplicates of samples. According to FDA guidelines, the maximum allowance for the CV for high potency drug among duplicates of dosages is 10%. The Results are shown in Table 1:

TABLE 1

Mn content in canine adult dry food with or without the inclusion of 3% of VNB

| | Mn (ppm; DMB) | |
|---|---|---|
| Sample duplicate No. | Control (0% VNB) | Test (3% VNB) |
| 1 | 19.4 | 34.7 |
| 2 | 22.7 | 41.0 |
| 3 | 19.2 | 34.4 |
| 4 | 19.6 | 35.6 |
| 5 | 20.6 | 38.2 |
| 6 | 20.7 | 38.5 |
| 7 | 19.4 | 34.8 |
| 8 | 21.0 | 41.0 |
| 9 | 18.3 | 33.9 |
| 10 | 22.1 | 41.1 |
| Average | 20.3 | 37.3 |
| Std Deviation | 1.38 | 2.96 |
| Coefficient of Variance | 6.8% | 7.9% |
| Mn fortification target | 0.0 | 14.7 |
| Expected Mn content | 20.3 | 35.0 |
| Averaged recovery rate (%) | — | 106.61% |

The dry VNBs contain 490 ppm of Mn on a dry matter basis. Therefore, inclusion of 3% of VNBs in a diet is expected to deliver 14.7 ppm of Mn in a diet, where the VNBs are evenly and accurately dispensed in an individual kibble. It can be seen from the results in Table 1 that the methods of the invention can evenly and accurately dispend small quantities of micronutrients among a pet food diet. As shown in Table 1, the Control diet contained an average of 20.3 ppm of Mn with a CV of 6.8% among 10 duplicates of samples prior to the VNB inclusion, while the Test diet contained an average of 37.3 ppm of Mn with a CV of 7.9% after the inclusion of 3% of VNBs. Respecting the intrinsic CV of 6.8% for the Mn distribution in the Control diet, the VNB process only added 1.1% of additional variability to the Test diet. Overall, according to FDA guideline, both conventional and the VNB methods for fortification of micronutrients in a pet food diet can be recognized as precise methods.

The accuracy of nutrient fortification is important to deliver efficacy of the fortified nutrient around the intended dosage level and can be expressed by the ratio of the amounts of actually delivered nutrient versus the intended fortification level or the recovery rate. As the 3% of VNB delivers 14.7 ppm of Mn to the Test diet, the Mn level in the finished Test diet is expected to be at 35.0 ppm. Respecting the averaged Mn content in the Test Diet is 37.3 ppm, the averaged recovery rate of Mn fortification among the Test diet is 106.6%, of which the 6.6% above the target fortification level is not only well within FDA's maximum tolerance (20%) for nutrient labeling but also is above the FDA's requirement for the minimum guaranty of the claimed fortification.

Thus, the results show that the methods of the invention are precise and accurate methods for fortifying delicate amounts of micronutrients in pet food products.

EXAMPLE 3

Nutrient Retention

As discussed above, the methods of the invention improve the retention of fortified micronutrients in a diet through nutrient protection and reduced thermal processing. By incorporating the VNBs into a diet through a side feeding device such as the tubular device described above, the VNBs bypass approximately 1.5 to 4.5 min of hot and wet process conditions in the pre-conditioner, and are therefore heat labile nutrients such as vitamins, carotenoids, antioxidants, etc. are expected to be shielded the from excessive exposure to thermal and hydrolytic conditions prior to extrusion so to improve the retention of micronutrients.

A nutrient retention study was carried out to compare the retention of ascorbic acid (vitamin C) in a dry kibble dog food formulation containing 2% or 4% of VNBs (Test diet) to that in a commercial diet fortified with vitamin C (Control diet). Vitamin C is one of the most heat labile vitamins, and is sensitive to heat, hydrolytic, and oxidative degradation; and is therefore a good indicator for examining the effects of processing on nutrient retention.

The study was designed to fortify similar amounts of vitamin C in either the Control or the VNB-included diets then compare the contents of residual vitamin C in between the finished foods. The Control diet was made from a commercial dry kibble formulation with fortification of 1,000 ppm of vitamin C provided as a powder additive. For the Test diets, vitamin C was fortified through inclusion of either 2% or 4% of VNBs in the diet. The vitamin C retention rate was determined by comparing the vitamin C content in the finished food after processing to that in the ingredient mix prior to processing. The results are shown below in Table 2.

TABLE 2

The Vitamin C contents in the Control and 2 Test diets on a dry matter basis (DMB).

| Sample | Control | | Test | | | |
|---|---|---|---|---|---|---|
| Sample Type | Ingredient Mix | Finished Food | Ingredient Mix | 100% VNB | 2% VNB*[a] | 4% VNB*[b] |
| Vitamin C (ppm) DMB | 1242 | 711 | 98 | 7987 | 321 | 422 |
| At 100% Recovery | | | | | 271 | 443 |
| % Vitamin C Retention | | 57.2 | | | 118.5 | 95.3 |

Note:
[a]The test diet contained 2% of VNB and 98% of Ingredient Mix.
[b]The test diet contained 4% of VNB and 96% of Ingredient Mix.

As shown in Table 2, the vitamin C in the ingredient mix of the Control diet was 1,242 ppm prior to the extrusion process and was 711 ppm in the finished food after processing. Therefore, the vitamin C retention rate for the Control diet was 57.2%. As the vitamin C content in VNBs was 7,987 ppm, the theoretical content of vitamin C in the Test diet containing either 2% or 4% of VNB was expected to be 271 or 443 ppm, respectively with the inclusion of the 98 ppm of vitamin C from the ingredient mix for the test diets. As the vitamin C content in finished Test diet containing either 2% or 4% VNBs was 321 ppm or 422 ppm, respectively, the vitamin C retention rates were 118.5% for the 2% VNBs included diet and 95.3% for the 4% VNBs included diet, respectively. The averaged vitamin retention rate of the Test diets was 106.9%, which was higher than that of the Control diet (57.2%). While the measurement of average retention values in excess of 100% for the Test sample suggests some degree of experimental variability, the results support that the VNBs protect the Vitamin C from any substantial degradation during processing. These results show that the methods of the invention improve the retention of micronutrients through encapsulation and avoidance of excessive thermal and hydration processing.

EXAMPLE 4

Palatability

Dogs prefer the food with inclusion of 4% of VNBs to the non-VNB included diet. A study was carried out to see whether inclusion of VNBs in a diet improves palatability. Canine adult dry food without or with the inclusion of either 2% or 4% of VNBs was processed as those mentioned previously. For a preliminary study, either the 2% or 4% VNBs included diet was presented as the Test food to a dog taste panel consisted of 25 dogs during a 2-day feeding session while the non-VNB included diet was presented as the Control food. The amounts of either the Control or Test food consumed by each dog panelist during the 2-day feeding session were collected and analyzed. The preference was assigned to the food with the higher amounts of consumption between the two. The intake ratio (IR) was determined by the ratio of the amounts of the Test food consumption versus the overall consumption for each panelist. The intake ratios were statistically analyzed using a Student T-test model. The palatability of food was expressed by the averaged intake ratio of the Test food along with the probability (p) value reported by the T-test. Win or loss is assigned to the Test food if its intake ratio is significantly higher or lower than that of the Control based on a 95% confidence level according to the distribution pattern of single tail T-values; otherwise, the palatability of Test food is in parity with the Control food.

It was interestingly observed from the preliminary study that the dog panelists preferred the Test food containing 4% of VNBs to the Control food at a ratio of 72 over 24 (or 3 to 1) with a significantly higher IR of 0.535 and a p value of 0.007 while the palatability of 2% VNB included diet was in parity with that of the Control food. To confirm such winning by the 4% VNB included diet, a confirmation study was conducted using a 2-day by 50-dog taste panel to verify whether different dog panelists would make similar choices. Therefore, a different but up-sized taste panel comprised of 50 dog panelists was used for the confirmation study. The very same foods were fed to the 50 dog panelists for 2 days. The results confirmed the observations from the preliminary study that dogs preferred the 4% VNB included diet to the non-VNB included control at a ratio of 69 over 29 (or 2.4 to 1) with a significantly higher IR of 0.581 at a p value of 0.01. The results of both studies are summarized in Table 3 below.

TABLE 3

Results of palatability tests

| Test No | Protocol | Test Food | Control Food | Verdict | Pref. | IR |
|---|---|---|---|---|---|---|
| 1 | 2-day by 25 dogs | K9 Adult 2% Bacon Bits | Canine Adult Corn Control | Parity p = 0.15 | 40/52 | 0.467 |
| 2 | | K9 Adult 4% Bacon Bits | 0 inclusion | Win p = 0.007 | 72/24 | 0.535 |
| 3 | 2-day by 50 dogs | | | Win p = 0.01 | 69/29 | 0.581 |

The results of the foregoing studies show that the methods of the invention provide a new approach to fortify micronutrients in a dry pet food diet by the inclusion of visible and identifiable nutrient bits on the surface or inside of dry pet food kibbles, which renders accurate and precise distributions of the designated doses of micronutrients among each handful of kibbles. The methods provide better retention for micronutrients than conventional methods because, inter alia, processing bypasses excessive exposure to hot and wet process conditions during the extrusion. In addition, the methods also provide dry pet food compositions having improved the palatability.

While the present invention has been described with reference to embodiments, it will be understood by those skilled in the art that various modifications and variations may be made therein without departing from the scope of the present invention as defined by the appended claims.

What is claimed is:

1. A pet food composition comprising a plurality of kibbles with one or more micronutrient particles incorporated therein,
    wherein the micronutrient particles are visually distinct and comprise one or more micronutrients and an extrudable binder,
    wherein the extrudable binder comprises rice and gluten,
    wherein the micronutrient particles comprise:
        brewers rice in an amount of from 45% to 55%;
        wheat gluten in an amount of from 35% to 45%;
        ascorbic acid in an amount of from 1% to 5%; and
        thiamine hydrochloride in an amount of from 1% to 5%,
    wherein the plurality of kibbles have a coefficient of variance for the content of the micronutrients of less than 10%, and
    wherein the plurality of kibbles are extruded.

2. The pet food composition of claim 1, wherein the micronutrient particles further comprise one or more micronutrients selected from antioxidants, minerals, vitamins, carotenoids, glucosamine, chondroitin sulfate, nutraceutical ingredients, nutrient supplements, medicines, or combinations thereof.

3. The pet food composition of claim 1 wherein the micronutrient particles are 0.5-5 mm in size.

4. The pet food composition of claim 1, wherein the micronutrient particles are delayed-release particles.

5. The pet food composition of claim 1, wherein the micronutrient particles comprise 1% to 10% by weight of the pet food composition.

6. The pet food composition of claim 1, wherein the micronutrient particles further comprise one one or more pigments.

7. The pet food composition of claim 1, wherein the micronutrient particles comprise one or more orally acceptable insoluble pigments in an amount effective to impart color to the micronutrient particle.

8. The pet food composition of claim 1, wherein the one or more micronutrient particles comprise at least 100 times the concentration of a particular micronutrient relative to the concentration of the particular micronutrient in the rest of the kibble.

* * * * *